United States Patent [19]
Nabika et al.

[11] Patent Number: 6,107,502
[45] Date of Patent: Aug. 22, 2000

[54] METHOD FOR PURIFYING TRANSITION METAL COMPOUND AND METHOD FOR PRODUCING THE SAME

[75] Inventors: Masaaki Nabika, Ichihara; Kotohiro Nomura, Ikoma, both of Japan

[73] Assignee: Sumitomo Chemical Company, Limited, Osaka, Japan

[21] Appl. No.: 09/168,996

[22] Filed: Oct. 9, 1998

[30] Foreign Application Priority Data

Oct. 13, 1997 [JP] Japan ................................. 9-278571

[51] Int. Cl.$^7$ .............................. C07F 17/00; C07F 7/00
[52] U.S. Cl. ................................ 556/11; 556/1; 556/7; 556/21; 556/53; 502/103; 502/117; 526/160; 526/943
[58] Field of Search ................... 556/11, 53, 1, 556/7, 21; 502/103, 117; 526/160, 943

[56] References Cited

U.S. PATENT DOCUMENTS

| | | | |
|---|---|---|---|
| 5,096,867 | 3/1992 | Canich | 502/103 |
| 5,302,733 | 4/1994 | Diefenbach et al. | 556/11 |
| 5,567,842 | 10/1996 | Izumisawa et al. | 562/486 |

FOREIGN PATENT DOCUMENTS

| | | |
|---|---|---|
| 0426643 A1 | 5/1991 | European Pat. Off. . |
| 0612769 A1 | 8/1994 | European Pat. Off. . |
| 289448-A7 | 5/1991 | Germany . |
| 93/08199 | 4/1993 | WIPO . |

OTHER PUBLICATIONS

Japanese Publication No. 07053581; Publication date Feb. 28, 1995, Abstract only.

P.A. Schweitzer, Handbook of separation techniques for chemical engineers/second edition, 1988 page(s) 2–172.

E. Muller, Methoden der organischen chemie (Houben–Weyl) Band I/1, 1958, p. 378.

Japanese Publication No. 63 139181 (A); Publication date Jun. 10, 1988—Abstract only.

*Primary Examiner*—Porfirio Nazario-Gonzalez
*Attorney, Agent, or Firm*—Birch, Stewart, Kolasch & Birch, LLP

[57] ABSTRACT

A method for purifying a transition metal compound, which comprises conducting crystallization of a transition metal compound from a solution containing the transition metal compound while stirring.

According to the present invention, it is possible to purify and produce efficiently a transition metal compound at high purity under industrially and economically advantageous conditions.

16 Claims, No Drawings

METHOD FOR PURIFYING TRANSITION METAL COMPOUND AND METHOD FOR PRODUCING THE SAME

BACKGROUND OF THE INVENTION

1. Field of the Invention

The present invention relates to a method for producing a purified transition metal compound which can be industrially used.

2. Description of the Related Arts

Transition metal compounds are useful as reaction reagents in a lot of organic synthesis reactions and catalysts, and currently widely used and investigated. Among other, specific transition metal complexes containing a group having a cyclopentadiene type anionic skeleton (so-called metallocene transition metal compounds), in particular, a compound of an early transition metal such as titanium, zirconium or the like is extremely effective as catalyst components for olefin polymerization, and development of the compounds including their utilization is widely studied.

In production of such transition metal compound, it is preferable to isolate and purify the compound obtained. When a solid transition metal compound containing impurities, which has not been purified is used as it is, there often is a reduction of activity or influence on composition distribution of the resulted polymer, which are guessed to be derived from the impurities.

In synthesis of laboratory level, the following method is often adopted: a reaction solid containing a transition metal compound is dissolved in a specific solvent or a mixed solvent composed of several solvents having different properties, and the mixture is allowed to stand still for a long period of time at normal temperature or with cooling to deposit a crystal onto the bottom or wall of a flask or the like for obtaining the intended transition metal compound of high purity. However, in the case of production on industrial scale, the above-described method in which a crystal is deposited on the inner wall of a reaction vessel, has not only a problem that taking out of the crystal is extremely difficult but also a problem that the apparatus used is injured when a crystal is taken out, therefore, industrial operation is extremely difficult.

SUMMARY OF THE INVENTION

An object of the present invention is to provide a method for purifying and producing a transition metal compound, which can be practiced even on industrial scale and is economically advantageous.

The present invention relates to a method for purifying a transition metal compound in which a solution containing the transition metal compound is subjected to crystallization while stirring, and a method for producing a purified transition metal compound, comprising a step for conducting the above-described purification method.

The present invention will be explained in detail below.

DETAILED DESCRIPTION OF THE INVENTION

The purification method of a transition metal compound of the present invention is a purification method in which a solution containing the transition metal compound is subjected to crystallization while stirring, and, for example, a purification method in which a solution (reaction solution) containing a crude product of the transition metal compound produced, a solution into which the transition metal compound containing impurities is dissolved, or the like is subjected to crystallization.

As a solvent for the transition metal compound, any solvent which dissolve the transition metal compound can be used, and, usually, a solvent used for crystallization is preferred. Specific examples of the solvent include aromatic hydrocarbon solvents such as benzene, toluene, xylene, mesitylene, chlorobenzene, dichlorobenzene and the like; aliphatic hydrocarbon solvents such as pentane, hexane, heptane, octane, petroleum ether and the like; etheral solvents such as tetrahydrofuran, dioxane, diethyl ether, diisopropyl ether, dimethoxyethane and the like; halogenated hydrocarbon solvents such as dichloromethane, dichloroethane, chloroform and the like.

These solvents are used alone or in combination of two or more. The amount of the solvent used is usually from 1 to 200 g/ml in terms of the weight of a transition metal compound per volume of a solvent. Excess amount of the solvent used causes not only reduction in volume efficiency but also increase in the amount of the compound remaining in the solution. Though the amount used varies depending on the temperature and the solubility of the compound, it is preferably in the range from 3 to 50 g/ml.

In the method for purifying a transition metal compound of the present invention, it is preferable that after a poor solvent is added to a solution containing the transition metal compound, crystallization is conducted while stirring.

Herein, the poor solvent means a solvent having lower solubility of a transition metal compound than that to the solvent used in the above-described solution containing a transition metal compound. It is impossible to define unconditionally which solvent is suitable as a poor solvent, however, in many transition metal compounds, an aromatic hydrocarbon solvent and/or aliphatic hydrocarbon solvent can be used as a poor solvent.

Regarding the combination of the above-described solvent for a solution containing a transition metal compound with a poor solvent, in a transition metal complex containing two groups having a cyclopentadiene type anionic skeleton (hereinafter, sometimes referred to as "bis Cp metallocene"), examples of the former solvent include, but not limited to, halogen-based solvents and the like, and examples of the latter poor solvent include, but not limited to, aromatic hydrocarbon solvents and the like. In a transition metal complex containing one group having a cyclopentadiene type anionic skeleton (hereinafter, sometimes referred to as "mono Cp metallocene"), examples of the former solvent include, but not limited to, aromatic hydrocarbon solvents, and examples of the latter poor solvent include, but not limited to, aliphatic hydrocarbon solvents.

The suitable amount of the poor solvent used is varied depending on the temperature and the solubility of a compound in the poor solvent, however, it is preferably in the range from 0.1 to 10-fold by volume, more preferably in the range from 0.1 to 3-fold by volume based on the amount of the above-described solvent for a solution containing a transition metal compound since excess amount of solvent used causes not only reduction in volume efficiency but also increase in the amount of the compound remaining in the solution.

In the method for purifying a transition metal compound of the present invention, the solution containing a transition metal compound is preferably concentrated prior to crystallization. As the concentration method, a method in which the solution is heated, a method in which the solution is heated under reduced pressure, and the like are listed.

In the method for purifying a transition metal compound of the present invention, crystallization of the transition metal compound is preferably carried out while stirring and cooling the solution containing the transition metal compound. The cooling temperature is not particularly restricted providing it is temperature usually suitable for crystallization, and preferably from −100 to 35° C., more preferably from −50 to 30° C., and most preferably in the range from −20 to 25° C. which is advantageous for industrial process.

In the method for purifying a transition metal compound of the present invention, it is preferable that a solution which has been prepared by dissolving the transition metal compound in a solvent in amount as small as possible at temperature as high as possible is cooled slowly, and subjected to crystallization while stirring and cooling. The temperature as high as possible means, depending on a solvent used, preferably a temperature in the range from 35 to 150° C., more preferably a temperature in the range from 40 to 100° C.

As the transition metal compound which can be applied to the present invention, early transition metal compounds are preferably listed, and among them, compounds having olefin polymerization ability are suitable.

As more preferable transition metal compounds, compounds of transition metal of III to V Groups of the Periodic Table of Elements are used. Here, specific examples of the III Group transition metal include scandium and yttrium, specific examples of the IV Group transition metal include titanium, zirconium and hafnium, specific examples of the V Group transition metal include vanadium, niobium and the like, and among them, IV Group transition metal compounds are most preferred.

As the transition metal compound having an olefin polymerization ability, so-called metallocene transition metal complexes and non-metallocene transition metal compounds are known and can be applied to the present invention, and preferably, metallocene transition metal complexes, namely, transition metal complexes containing at least one group having a cyclopentadiene type anionic skeleton are suitable.

The transition metal compound used in the present invention is preferably a transition metal complex represented by the following general formulas (1) to (5):

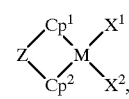 (1)

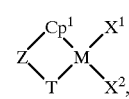 (2)

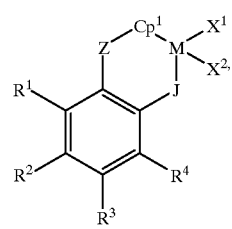 (3)

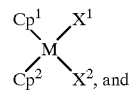 (4)

 (5)

(wherein M represents a transition metal atom of IV Group in the Periodic Table of Elements; $Cp^1$ and $Cp^2$ represent each independently a group having a cyclopentadiene type anion skeleton; $X^1$, $X^2$, $R^1$, $R^2$, $R^3$ and $R^4$ represent each independently a hydrogen atom, a halogen atom, an alkyl group having 1 to 20 carbon atoms, an aralkyl group having 7 to 20 carbon atoms, an aryl group having 6 to 20 carbon atoms, a silyl group having 1 to 20 carbon atoms, an alkoxy group having 1 to 20 carbon atoms, an aralkyloxy group having 7 to 20 carbon atoms, an aryloxy group having 6 to 20 carbon atoms or an amino group having 2 to 20 carbon atoms; $R^1$, $R^2$, $R^3$ and $R^4$ may optionally be connected to form a ring; Z represents a divalent group represented by $SiR'_2$, $CR'_2$, $SiR'_2SiR'_2$, $CR'_2CR'_2$, $CR'=CR'$, $CR'_2SiR'_2$, $GeR'_2$ or $BR'$ (wherein, R' represents, in each case, a hydrogen atom, a halogen atom, an alkyl group having 1 to 20 carbon atoms, an alkenyl group having 2 to 20 carbon atoms, an aralkyl group having 7 to 20 carbon atoms, an aryl group having 6 to 20 carbon atoms, a silyl group having 1 to 20 carbon atoms, an alkoxy group having 1 to 20 carbon atoms, an aralkyloxy group having 7 to 20 carbon atoms, an aryloxy group having 6 to 20 carbon atoms which may be substituted or an amino group having 2 to 20 carbon atoms. When there are a plurality of R's, they may be combined to make a ring.); T represents a divalent group represented by —O—, —S—, —$NR^5$— or —$PR^6$— (wherein, $R^5$ and $R^6$ represent each independently an alkyl group having 1 to 20 carbon atoms, an aralkyl group having 7 to 20 carbon atoms, an aryl group having 6 to 20 carbon atoms or a silyl group having 1 to 20 carbon atoms); J represents an atom of XVI Group in the Periodic Table of Elements; and Q represents —$OR^7$, —$SR^8$, —$NR^9R^{10}$, or $PR^{11}R^{12}$ (wherein $R^7$, $R^8$, $R^9$, $R^{10}$, $R^{11}$ and $R^{12}$ represent each independently an alkyl group having 1 to 20 carbon atoms, an aralkyl group having 7 to 20 carbon atoms, an aryl group having 6 to 20 carbon atoms or a silyl group having 1 to 20 carbon atoms)).

In the above-described general formulas (1) to (5), M represents a transition metal atom of IV Group in the Periodic Table of Elements (IUPAC Inorganic Chemical Nomenclature, Revised Edition 1989), and examples thereof include a titanium atom, zirconium atom, hafnium atom and the like.

Examples of the groups having a cyclopentadiene type anionic skeleton shown as Cp1 and Cp2 include $\eta^5$-cyclopentadienyl group, $\eta^5$-methylcyclopentadienyl group, $\eta^5$-dimethylcyclopentadienyl group, $\eta^5$-trimethylcyclopentadienyl group, $\eta^5$-tetramethylcyclopentadienyl group, $\eta^5$-pentamethylcyclopentadienyl group(in compounds represented by the general formulas (4) and (5)), $\eta^5$-ethylcyclopentadienyl group, $\eta^5$-n-propylcyclopentadienyl group, $\eta^5$-isopropylcyclopentadienyl group, $\eta^5$-n-butylcyclopentadienyl group, $\eta^5$-sec-butylcyclopentadienyl group, $\eta^5$-tert-butylcyclopentadienyl group, $\eta^5$-n-pentylcyclopentadienyl group, $\eta^5$-neopentylcyclopentadienyl group, $\eta^5$-n-hexylcyclopentadienyl group, $\eta^5$-n-octylcyclopentadienyl group, $\eta^5$-phenylcyclopentadienyl group, $\eta^5$-naphthylcyclopentadienyl group, $\eta^5$-trimethylsilylcyclopentadienyl group, $\eta^5$-triethylsilylcyclopentadienyl group, $\eta^5$-tert-butyldimethylsilylcyclopentadienyl group, $\eta^5$-indenyl group, $\eta^5$-methylindenyl group, $\eta^5$-dimethylindenyl group, $\eta^5$-ethylindenyl group, $\eta^5$-n-propylindenyl group, $\eta^5$-isopropylindenyl group, $\eta^5$-n-butylindenyl group, $\eta^5$-sec-butylindenyl group, $\eta^5$-tert-butylindenyl group, $\eta^5$-n-pentylindenyl group, $\eta^5$-neopentylindenyl group, $\eta^5$-n-hexylindenyl group, $\eta^5$-n-octylindenyl group, $\eta^5$-n-decylindenyl group, $\eta^5$-phenylindenyl group, $\eta^5$-methylphenylindenyl group, $\eta^5$-naphthylindenyl group, $\eta^5$-trimethylsilylindenyl group, $\eta^5$-triethylsilylindenyl group, $\eta^5$-tert-butyldimethylsilylindenyl group, $\eta^5$-tetrahydroindenyl group, $\eta^5$-fluorenly group, $\eta^5$-methylfluorenly group, $\eta^5$-dimethylfluorenly group, $\eta^5$-ethylfluorenly group, $\eta^5$-diethylfluorenly group, $\eta^5$-n-propylfluorenly group, $\eta^5$-di-n-propylfluorenly group, $\eta^5$-isopropylfluorenly group, $\eta^5$-diisopropylfluorenly group, $\eta^5$-n-butylfluorenly group, $\eta^5$-sec-butylfluorenly group, $\eta^5$-tert-butylfluorenly group, $\eta^5$-di-n-butylfluorenly group, $\eta^5$-di-sec-butylfluorenly group, $\eta^5$-di-tert-butylfluorenly group, $\eta^5$-n-pentylfluorenly group, $\eta^5$-neopentylfluorenly group, $\eta^5$-n-hexylfluorenly group, $\eta^5$-n-octylfluorenly group, $\eta^5$-n-decylfluorenly group, $\eta^5$-n-dodecylfluorenly group, $\eta^5$-phenylfluorenly group, $\eta^5$-di-phenylfluorenly group, $\eta^5$-methylphenylfluorenly group, $\eta^5$-naphthylfluorenly group, $\eta^5$-trimethylsilylfluorenly group, $\eta^5$-bis-trimethylsilylfluorenly group, $\eta^5$-triethylsilylfluorenly group, $\eta^5$-tert-butyldimethylsilylfluorenly group and the like, and preferable examples thereof include $\eta^5$-cyclopentadienyl group, $\eta^5$-methylcyclopentadienyl group, $\eta^5$-tert-butylcyclopentadienyl group, $\eta^5$-tetramethylcyclopentadienyl group, $\eta^5$-indenyl group, $\eta^5$-fluorenyl group and the like. In the general formula (1) or (4), Cp1 and Cp2 may be the same or different.

Example of the halogen atom in $X^1$, $X^2$, $R^1$, $R^2$, $R^3$ or $R^4$ include a fluorine atom, chlorine atom, bromine atom and iodine atom.

Examples of the alkyl group having 1 to 20 carbon atoms in $X^1$, $X^2$, $R^1$, $R^2$, $R^3$ or $R^4$ include a methyl group, ethyl group, n-propyl group, isopropyl group, n-butyl group, sec-butyl group, tert-butyl group, n-pentyl group, isopenthyl group, neopentyl group, n-hexyl group, n-octyl group, n-decyl group, n-dodecyl group, n-pentadecyl group, n-eicosyl group and the like, and preferable examples thereof include a methyl group, ethyl group, isopropyl group, tert-butyl group, n-pentyl group isopenthyl group, and neopentyl group.

These alkyl groups may be substituted with a halogen atom such as a fluorine atom, chlorine atom, bromine atom or iodine atom.

Examples of the alkyl group having 1 to 20 carbon atoms substituted with a halogen atom include a fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobuthyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group, perbromoeicosyl group and the like.

These alkyl groups may be partially substituted with an alkoxy group such as a methoxy group, ethoxy group or the like, an aryloxy group such as phenoxy group or the like, an aralkyloxy group such as benzyloxy group, or the like.

Examples of the aralkyl group having 7 to 20 carbon atoms in $X^1$, $X^2$, $R^1$, $R^2$, $R^3$ or $R^4$ include a benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (4,6-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-tetradecylphenyl)methyl group, naphthylmethyl group, anthracenylmethyl group and the like, and a benzyl group is preferable.

These aralkyl groups may be substituted with a halogen atom such as a fluorine atom, chlorine atom, bromine atom, or iodine atom, an alkoxy group such as a methoxy group, ethoxy group or the like, an aryloxy group such as a phenoxy group or the like, an aralkyloxy group such as a benzyloxy, or the like.

Examples of the aryl group having 6 to 20 carbon atoms in $X^1$, $X^2$, $R^1$, $R^2$, $R^3$ or $R^4$ include a phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopenthylphenyl group, n-hexylphenyl group, n-octylphenyl group, n-decylphenyl group, n-dodecylphenyl group, n-tetradecylphenyl group, naphthyl group, anthracenyl group and the like, and a phenyl group is preferable.

These aryl groups may be substituted with a halogen atom such as a fluorine atom, chlorine atom, bromine atom or iodine atom, an alkoxy group such as a methoxy group, ethoxy group or the like, an aryloxy group such as a phenoxy group or the like, an aralkyloxy group such as a benzyloxy group, or the like.

The silyl group having 1 to 20 carbon atoms in $X^1$, $X^2$, $R^1$, $R^2$, $R^3$ or $R^4$ is a silyl group substituted with a hydrocarbon group, and examples of the hydrocarbon group include alkyl groups having 1 to 10 carbon atoms such as a methyl group, ethyl group, n-propyl group, isopropyl group, n-butyl group, sec-butyl group, tert-butyl group, isobutyl group, n-pentyl group, n-hexyl group, cyclohexyl group and the like, an aryl group such as a phenyl group, and the like. Examples of the silyl group having 1 to 20 carbon atoms include mono-substituted silyl groups having 1 to 20 carbon atoms such as a methylsilyl group, ethylsilyl group, phenylsilyl group and the like, di-substituted silyl groups having 2 to 20 carbon atoms such as a dimethylsilyl group, diethylsilyl group, diphenylsilyl group and the like, tri-substituted silyl groups having 3 to 20 carbon atoms such as a trimethylsilyl group, triethylsilyl group, tri-n-propylsilyl group, triisopropylsilyl group, tri-n-butylsilyl group, tri-sec-butylsilyl group, tri-tert-butylsilyl group, triisobutylsilyl group, tert-butyldimethylsilyl group, tri-n-pentylsilyl group, tri-n-hexylsilyl group, tricyclohexylsilyl group, triphenylsilyl group and the like, and preferably examples thereof include a trimethylsilyl group, tert-butyldimethylsilyl group and triphenylsilyl group.

These silyl groups may be substituted with a halogen atom such as a fluorine atom, chlorine atom, bromine atom or iodine atom, an alkoxy group such as a methoxy group, ethoxy group or the like, an aryloxy group such as a phenoxy group or the like, an aralkyloxy group such as benzyloxy, or the like.

Examples of the alkoxy group having 1 to 20 carbon atoms in $X^1$, $X^2$, $R^1$, $R^2$, $R^3$ or $R^4$ include a methoxy group, ethoxyl group, n-propoxy group, isopropoxy group, n-butoxy group, sec-butoxy group, t-butoxy group, n-pentoxy group, neopentoxy group, n-hexoxy group, n-octoxy group, n-dodecoxy group, pentadecoxy, n-itacoxy group and the like, and preferably examples thereof include a methoxy group, ethoxy group and t-butoxy group.

These alkoxy groups may be substituted with a halogen atom such as a fluorine atom, chlorine atom, bromine atom or iodine atom, an alkoxy group such as a methoxy group, ethoxy group or the like, an aryloxy group such as a phenoxy group or the like, an aralkyloxy group such as a benzyloxy group, or the like.

Examples of the aralkyloxy group having 7 to 20 carbon atoms in $X^1$, $X^2$, $R^1$, $R^2$, $R^3$ or $R^4$ include a benzyloxy group, (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (3,5-dimethylphenyl)methoxy group, (2,3,4-trimethylphenyl)methoxy group, (2,3,5-trimethylphenyl)methoxy group, (2,3,6-trimethylphenyl)methoxy group, (2,4,5-trimethylphenyl)methoxy group, (2,4,6-trimethylphenyl)methoxy group, (3,4,5-trimethylphenyl)methoxy group, (2,3,4,6-tetramethylphenyl)methoxy group, (2,3,5,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-hexylphenyl)methoxy group, (n-octylphenyl)methoxy group, (n-decylphenyl)methoxy group, (n-tetradecylphenyl)methoxy group, naphthylmethoxy group, anthracenylmethoxy group and the like, and a benzyloxy group is preferable.

These aralkyloxy groups may be substituted with a halogen atom such as a fluorine atom, chlorine atom, bromine atom or iodine atom, an alkoxy group such as a methoxy group, ethoxy group or the like, an aryloxy group such as a phenoxy group or the like, an aralkyloxy group such as a benzyloxy group, or the like.

Examples of the aryloxy group having 1 to 20 carbon atoms in $X^1$, $X^2$, $R^1$, $R^2$, $R^3$ or $R^4$ include aryloxy groups having 6 to 20 carbon atoms such as a phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, naphthoxy group, anthracenoxy group and the like.

These aryloxy groups may be substituted with a halogen atom such as a fluorine atom, chlorine atom, bromine atom or iodine atom, an alkoxy group such as a methoxy group, ethoxy group or the like, an aryloxy group such as a phenoxy group or the like, an aralkyloxy group such as a benzyloxy group, or the like.

The di-substituted amino group having 2 to 20 carbon atoms in $X^1$, $X^2$, $R^1$, $R^2$, $R^3$ or $R^4$ is an amino group substituted with two hydrocarbon groups, and examples of the hydrocarbon group include alkyl groups having 1 to 10 carbon atoms such as a methyl group, ethyl group, n-propyl group, isopropyl group, n-butyl group, sec-butyl group, tert-butyl group, isobutyl group, n-pentyl group, n-hexyl group, cyclohexyl group and the like, an aryl group such as a phenyl group and the like, and the like. Examples of the di-substituted amino group having 1 to 10 carbon atoms include a dimethylamino group, diethylamino group, di-n-propylamino group, diisopropylamino group, di-n-butylamino group, di-sec-butylamino group, di-tert-butylamino group, di-isobutylamino group, tert-butylisopropylamino group, di-n-hexylamino group, di-n-octylamino group, di-n-decylamino group, diphenylamino group, bistrimethylsilylamino group, bis-tert-butyldimethylsilylamino group and the like, and a dimethylamino group and diethylamino group are preferable.

$R^1$, $R^2$, $R^3$ and $R^4$ may optionally be connected to form a ring.

$R^1$, $R^2$, $R^3$ and $R^4$ preferably represent each independently a hydrogen atom, a halogen atom, an alkyl group having 1 to 20 carbon atoms, an aryl group having 6 to 20 carbon atoms, an alkoxy group having 1 to 20 carbon atoms or a silyl group having 1 to 20 carbon atoms, wherein these groups may be substituted with a halogen atom, an alkoxy group, an aryloxy group, an aralkyloxy group or the like, and more preferably a hydrogen atom, chlorine atom, methyl group, amyl group, tert-butyl group, phenyl group, methoxy group, trimethylsilyl group, or tert-butyldimethylsilyl group.

$X^1$ and $X^2$ preferably represent each independently a halogen atom, an alkyl group having 1 to 20 carbon atoms, an aralkyl group having 7 to 20 carbon atoms, an alkoxy group having 1 to 20 carbon atoms, an aralkyloxy group having 7 to 20 carbon atoms, or an aryloxy group having 6 to 20 carbon atoms, wherein these groups may be substituted with a halogen atom, an alkoxy group, an aryloxy group, an aralkyloxy group or the like.

Z represents a divalent group represented by $SiR'_2$, $CR'_2$, $SiR'_2SiR'_2$, $CR'_2CR'_2$, $CR'=CR'$, $CR'_2SiR'_2$, $GeR'_2$ or $BR'$ (wherein, R' represents, in each case, a hydrogen atom, a halogen atom, an alkyl group having 1 to 20 carbon atoms, an alkenyl group having 2 to 20 carbon atoms, an aralkyl group having 7 to 20 carbon atoms, an aryl group having 6 to 20 carbon atoms, a silyl group having 1 to 20 carbon atoms, an alkoxy group having 1 to 20 carbon atoms, an aralkyloxy group having 7 to 20 carbon atoms, an aryloxy group having 6 to 20 carbon atoms or a di-substituted amino group having 2 to 20 carbon atoms, wherein these groups may be substituted with a halogen atom, an alkoxy group, an aryloxy group, an aralkyloxy group or the like. When apluralityof R's exist, they may be connected to form a ring.).

The halogen atom, alkyl group having 1 to 20 carbon atoms, aralkyl group having 7 to 20 carbon atoms, aryl group having 6 to 20 carbon atoms, silyl group having 1 to 20 carbon atoms, alkoxy group having 1 to 20 carbon atoms, aralkyloxy group having 7 to 20 carbon atoms, aryloxy group having 6 to 20 carbon atoms and di-substituted amino group having 2 to 20 carbon atoms as R' are the same as described above.

When a plurality of R's exist, they may be connected to form a ring, and examples of the R's include alkylene groups such as a tetramethylenediyl group, pentamethylenediyl group and the like.

R' represents preferably a hydrogen atom, said alkyl group, aryl group, alkoxy group or alkylene group, and more preferably a hydrogen atom, methyl group, ethyl group, phenyl group, methoxy group, tetramethylenediyl group or pentamethylenediyl group.

Specific examples of Z include dimethylsilylene, ethylmethylsilylene, diethylsilylene, methylphenylsilylene, diphenylsilylene, dimethoxysilylene, methylene, ethylidene, isopropylene, ethylmethylmethylene, diethylmethylene, methylphenylmethylene, diphenylmethylene, cyclopentene, cyclohexene, tetraethyldisilylene, tetraphenyldisilylene, ethylene, tetramethylethylene, tetraphenylethylene, dimethylgermilene, diphenylgermilene, methylborene, phenylborene and the like, and among these, dimethylsilylene, diphenylsilylene, divinylsilylene, methylene, isopropylene, diphenylmethylene and ethylene are preferable.

T represents a divalent group represented by —O—, —S—, —NR$^5$— or —PR$^6$—(wherein, R$^5$ and R$^6$ represent each independently an alkyl group having 1 to 20 carbon atoms, an aralkyl group having 7 to 20 carbon atoms, an aryl group having 6 to 20 carbon atoms or a silyl group having 1 to 20 carbon atoms, wherein these groups may be substituted with a halogen atom, an alkoxy group, an aryloxy group, an aralkyloxy group or the like).

The alkyl group having 1 to 20 carbon atoms, aralkyl group having 7 to 20 carbon atoms, aryl group having 6 to 20 carbon atoms and silyl group having 1 to 20 carbon atoms as R$^5$ or R$^6$ are the same as described above. R$^5$ and R$^6$ represent, each independently, preferably an alkyl group or aryl group, more preferably a methyl group, ethyl group, n-propyl group, iso-propyl group, tert-butyl group, cyclohexyl group or phenyl group.

The T is preferably a divalent group represented by —O— or —NR$^5$—.

Q represents a divalent group represented by —OR$^7$, —SR$^8$, —NR$^9$R$^{10}$ or —PR$^{11}$R$^{12}$ (wherein, R$^7$ to R$^{12}$ represent each independently an alkyl group having 1 to 20 carbon atoms, an aralkyl group having 7 to 20 carbon atoms, an aryl group having 6 to 20 carbon atoms or a silyl group having 1 to 20 carbon atoms, wherein these groups may be substituted with a halogen atom, an alkoxy group, an aryloxy group, an aralkyloxy group or the like).

The alkyl group having 1 to 20 carbon atoms, aralkyl group having 7 to 20 carbon atoms, aryl group having 6 to 20 carbon atoms and silyl group having 1 to 20 carbon atoms as R$^7$ to R$^{12}$ are the same as described above. R$^7$ to R$^{12}$ represent, each independently, preferably the alkyl group or aryl group, more preferably a methyl group, ethyl group, n-propyl group, iso-propyl group, tert-butyl group, cyclohexyl group or phenyl group.

The Q is preferably a group represented by —OR$^7$ or —NR$^9$R$^{10}$.

R$^9$ and R$^{10}$, and R$^{11}$ and R$^{12}$ may optionally be connected to each other to form a ring.

J is an atom of VXI Group in the Periodic Table of Elements, and examples thereof include an oxygen atom, sulfur atom, selenium atom and the like, and among these, an oxygen atom is most preferable.

Specific examples of the compound represented by the above-described general formula (1) include transition metal complexes such as methylenebis(cyclopentadienyl)titanium dichloride, isopropylideneibis (cyclopentadienyl)titanium dichloride, dimethylsilylenebis(cyclopentadienyl)titanium dichloride, diphenylsilylenebis(cyclopentadienyl)titanium dichloride, methylenebis (methylcyclopentadienyl) titaniumdichloride, isopropylidenebis (methylcyclopentadienyl)titanium dichloride, dimethylsilylenebis(methylcyclopentadienyl)titanium dichloride, diphenylsilylenebis(methylcyclopentadienyl) titanium dichloride, methylenebis (dimethylcyclopentadienyl)titanium dichloride, isopropylidenebis(dimethylcyclopentadienyl)titanium dichloride, dimethylsilylenebis(dimethylcyclopentadienyl) titanium dichloride, diphenylsilylenebis (dimethylcyclopentadienyl)titanium dichloride, methylenebis(trimethylcyclopentadienyl)titanium dichloride, isopropylidenebis(trimethylcyclopentadienyl) titanium dichloride, dimethylsilylenebis (trimethylcyclopentadienyl)titanium dichloride, diphenylsilylenebis(trimethylcyclopentadienyl)titanium dichloride, methylenebis(tetramethylcyclopentadienyl) titanium dichloride, isopropylidenebis (tetramethylcyclopentadienyl)titanium dichloride, dimethylsilylenebis(tetramethylcyclopentadienyl) titanium dichloride, diphenylsilylenebis (tetramethylcyclopentadienyl) titanium dichloride, methylenebis(ethylcyclopentadienyl)titanium dichloride, isopropylidenebis(ethylcyclopentadienyl)titanium dichloride, dimethylsilylenebis(ethylcyclopentadienyl) titanium dichloride, diphenylsilylenebis (ethylcyclopentadienyl)titanium dichloride, methylenebis (n-butylcyclopentadienyl)titanium dichloride, isopropylidenebis(n-butylcyclopentadienyl)titanium dichloride, dimethylsilylenebis(n-butylcyclopentadienyl) titanium dichloride, diphenylsilylenebis(n-butylcyclopentadienyl)titanium dichloride, methylenebis (tert-butylcyclopentadienyl)titanium dichloride, isopropylidenebis(tert-butylcyclopentadienyl)titanium dichloride, dimethylsilylenebis(tert-butylcyclopentadienyl) titanium dichloride, diphenylsilylenebis(tert-butylcyclopentadienyl)titanium dichloride, methylenebis (indenyl)titanium dichloride, isopropylidenebis(indenyl) titanium dichloride, ethylenebis(indenyl)titanium dichloride, dimethylsilylenebis(indenyl)titanium dichloride, diphenylsilylenebis(indenyl)titanium dichloride, methylenebis(tetrahydroindenyl)titanium dichloride, isopropylidenebis (tetrahydroindenyl)titanium dichloride, ethylenebis(tetrahydroindenyl)titanium dichloride, dimethylsilylenebis(tetrahydroindenyl)titanium dichloride, diphenylsilylenebis(tetrahydroindenyl)titanium dichloride, methylene(cyclopentadienyl)(fluorenyl)titanium dichloride, isopropylidene(cyclopentadienyl)(fluorenyl)titanium dichloride, dimethylsilylene(cyclopentadienyl)(fluorenyl) titanium dichloride, diphenylsilylene(cyclopentadienyl) (fluorenyl)titanium dichloride, methylene(cyclopentadienyl) (dimethylfluorenyl)titanium dichloride, isopropylidene (cyclopentadienyl)(dimethylfluorenyl) titanium dichloride, dimethylsilylene(dimethylcyclopentadienyl)(fluorenyl) titanium dichloride, diphenylsilylene (dimethylcyclopentadienyl)(fluorenyl) titanium dichloride, methylene(indenyl)(fluorenyl)titanium dichloride, isopropylidene(indenyl)(fluorenyl)titanium dichloride, dimethylsilylene(indenyl)(fluorenyl)titanium, compounds wherein titanium in these compounds replaced by zirconium or hafnium, compounds wherein dichloride in these compounds is replaced by diiodide, bis(dimethylamide), bis (diethylamide), di-n-butoxide, diisopropoxide, dimethoxide or diphenoxide and the like.

Specific examples of the compound represented by the above-described general formula (2) include transition metal complexes such as dimethylsilylene(methylamide) (cyclopentadienyl)titanium dichloride, dimethylsilylene (ethylamide)(cyclopentadienyl)titanium dichloride, dimethylsilylene(n-propylamide)(cyclopentadienyl) titanium dichloride, dimethylsilylene(isopropylamide) (cyclopentadienyl) titanium dichloride, dimethylsilylene(t-butylamide)(cyclopentadienyl)titanium dichloride, dimethylsilylene(phenylamide)(cyclopentadienyl)titanium dichloride, dimethylsilylene(cyclohexylamide) (cyclopentadienyl)titanium dichloride, compounds wherein cyclopentadienyl in these compounds is replaced by methylcyclopentadienyl, dimethylcyclopentadienyl, trimethylcyclopentadienyl, tetramethylcyclopentadienyl, ethylcyclopentadienyl, n-propylcyclopentadienyl, isopropylcyclopentadienyl, sec-butylcyclopentadienyl, isobutylcyclopentadienyl, tert-butylcyclopentadienyl, di-tert-butylcyclopentadienyl, tert-butyldimethylsilylcyclopentadienyl, phenylcyclopentadienyl, methylindenyl or phenylindenyl, compounds wherein dimethylsilylene in these compounds is replaced by diethylsilylene, diephenylsilylene, dimethoxysilylene, methylene, ethylene or isopropylidene, compounds wherein titanium in these compounds is replaced by zirconium or hafnium, compounds wherein dichloride in these compounds is replaced by dibromide, diiodide, bis(dimethylamide), bis(diethylamide), di-n-butoxide or diisopropoxide, and the like.

Specific examples of the compound represented by the above-described general formula (3) include transition metal compounds such as methylene(cyclopentadienyl) (3,5-dimethyl-2-phenoxy)titanium dichloride, methylene (cyclopentadienyl)(3-tert-butyl-2-phenoxy)titanium dichloride, methylene(cyclopentadienyl)(3-tert-butyl-5-methyl-2-phenoxy)titanium dichloride, methylene (cyclopentadienyl)(3-phenyl-2-phenoxy)titanium dichloride, methylene(cyclopentadienyl)(3-tert-butyldimethylsilyl-5-methyl-2-phenoxy)titanium dichloride, methylene(cyclopentadienyl)(3-trimethylsilyl-5-methyl-2-phenoxy)titanium dichloride, methylene (cyclopentadienyl)(3-tert-butyl-5-methoxy-2-phenoxy) titanium dichloride, methylene(cyclopentadienyl)(3-tert-butyl-5-chloro-2-phenoxy)titanium dichloride, methylene (methylcyclopentadienyl)(3,5-dimethyl-2-phenoxy) titanium dichloride, methylene(methylcyclopentadienyl)(3-tert-butyl-2-phenoxy)titanium dichloride, methylene (methylcyclopentadienyl)(3-tert-butyl-5-methyl-2-phenoxy)titanium dichloride, methylene (methylcyclopentadienyl)(3-phenyl-2-phenoxy)titanium dichloride, methylene(methylcyclopentadienyl)(3-tert-butyldimethylsilyl-5-methyl-2-phenoxy)titanium dichloride, methylene(methylcyclopentadienyl)(3-trimethylsilyl-5-methyl-2-phenoxy)titanium dichloride, methylene(methylcyclopentadienyl)(3-tert-butyl-5-methoxy-2-phenoxy)titanium dichloride, methylene (methylcyclopentadienyl)(3-tert-butyl-5-chloro-2-phenoxy) titanium dichloride, methylene(t-butylcyclopentadienyl)(3,5-dimethyl-2-phenoxy)titanium dichloride, methylene(t-butylcyclopentadienyl)(3-tert-butyl-2-phenoxy)titanium dichloride, methylene(t-butylcyclopentadienyl)(3-tert-butyl-5-methyl-2-phenoxy)titanium dichloride, methylene (t-butylcyclopentadienyl)(3-phenyl-2-phenoxy)titanium dichloride, methylene(t-butylcyclopentadienyl)(3-tert-butyldimethylsilyl-5-methyl-2-phenoxy)titanium dichloride, methylene(t-butylcyclopentadienyl)(3-trimethylsilyl-5-methyl-2-phenoxy)titanium dichloride, methylene(t-butylcyclopentadienyl)(3-tert-butyl-5-methoxy-2-phenoxy)titanium dichloride, methylene(t-butylcyclopentadienyl)(3-tert-butyl-5-chloro-2-phenoxy) titanium dichloride, methylene (tetramethylcyclopentadienyl)(3,5-dimethyl-2-phenoxy) titanium dichloride, methylene (tetramethylcyclopentadienyl)(3-tert-butyl-2-phenoxy) titanium dichloride, methylene (tetramethylcyclopentadienyl)(3-tert-butyl-5-methyl-2-phenoxy)titanium dichloride, methylene (tetramethylcyclopentadienyl)(3-phenyl-2-phenoxy) titanium dichloride, methylene (tetramethylcyclopentadienyl)(3-tert-butyldimethylsilyl-5-methyl-2-phenoxy)titanium dichloride, methylene (tetramethylcyclopentadienyl)(3-trimethylsilyl-5-methyl-2-phenoxy)titanium dichloride, methylene (tetramethylcyclopentadienyl)(3-tert-butyl-5-methoxy-2-phenoxy)titanium dichloride, methylene (tetramethylcyclopentadienyl)(3-tert-butyl-5-chloro-2-phenoxy)titanium dichloride, methylene (trimethylsilylcyclopentadienyl)(3,5-dimethyl-2-phenoxy) titanium dichloride, methylene (trimethylsilylcyclopentadienyl)(3-tert-butyl-2-phenoxy) titanium dichloride, methylene (trimethylsilylcyclopentadienyl)(3-tert-butyl-5-methyl-2-phenoxy)titanium dichloride, methylene (trimethylsilylcyclopentadienyl)(3-phenyl-2-phenoxy) titanium dichloride, methylene (trimethylsilylcyclopentadienyl)(3-tert-butyldimethylsilyl-5-methyl-2-phenoxy)titanium dichloride, methylene (trimethylsilylcyclopentadienyl)(3-trimethylsilyl-5-methyl-2-phenoxy)titanium dichloride, methylene (trimethylsilylcyclopentadienyl)(3-tert-butyl-5-methoxy-2-phenoxy)titanium dichloride, methylene (trimethylsilylcyclopentadienyl)(3-tert-butyl-5-chloro-2-phenoxy)titanium dichloride, methylene(fluorenyl)(3,5-dimethyl-2-phenoxy)titanium dichloride, methylene (fluorenyl)(3-tert-butyl-2-phenoxy)titanium dichloride, methylene(fluorenyl)(3-tert-butyl-5-methyl-2-phenoxy) titanium dichloride, methylene(fluorenyl)(3-phenyl-2-phenoxy)titanium dichloride, methylene(fluorenyl)(3-tert-butyldimethylsilyl-5-methyl-2-phenoxy)titanium dichloride, methylene(fluorenyl)(3-trimethylsilyl-5-methyl- 2-phenoxy)titanium dichloride, methylene(fluorenyl)(3-tert-butyl-5-methoxy-2-phenoxy)titanium dichloride, methylene(fluorenyl)(3-tert-butyl-5-chloro-2-phenoxy)titanium dichloride, isopropylidene(cyclopentadienyl)(3,5-dimethyl-2-phenoxy)titanium dichloride, isopropylidene(cyclopentadienyl)(3-tert-butyl-2-phenoxy)titanium dichloride, isopropylidene(cyclopentadienyl)(3-tert-butyl-5-methyl-2-phenoxy)titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene(cyclopentadienyl)(3-trimethylsilyl-5-methyl-2-phenoxy)titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene(methylcyclopentadienyl)(3-tert-butyl-2-phenoxy)titanium dichloride, isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene(methylcyclopentadienyl)(3-tert-butyldimethylsilyl-5-methyl-2-phenoxy)titanium dichloride, isopropylidene(methylcyclopentadienyl)(3-trimethylsilyl-5-methyl-2-phenoxy)titanium dichloride, isopropylidene(methylcyclopentadienyl)(3-tert-butyl-5-methoxy-2-phenoxy)titanium dichloride, isopropylidene(methylcyclopentadienyl)(3-tert-butyl-5-chloro-2-phenoxy)titanium dichloride, isopropylidene(t-butylcyclopentadienyl)(3,5-dimethyl-2-phenoxy)titanium dichloride, isopropylidene(t-butylcyclopentadienyl)(3-tert-butyl-2-phenoxy)titanium dichloride, isopropylidene(t-butylcyclopentadienyl)(3-tert-butyl-5-methyl-2-phenoxy)titanium dichloride, isopropylidene(t-butylcyclopentadienyl)(3-phenyl-2-phenoxy)titanium dichloride, isopropylidene(t-butylcyclopentadienyl)(3-tert-butyldimethylsilyl-5-methyl-2-phenoxy)titanium dichloride, isopropylidene(t-butylcyclopentadienyl)(3-trimethylsilyl-5-methyl-2-phenoxy)titanium dichloride, isopropylidene(t-butylcyclopentadienyl)(3-tert-butyl-5-methoxy-2-phenoxy)titanium dichloride, isopropylidene(t-butylcyclopentadienyl)(3-tert-butyl-5-chloro-2-phenoxy)titanium dichloride, isopropylidene(tetramethylcyclopentadienyl)(3,5-dimethyl-2-phenoxy)titanium dichloride, isopropylidene(tetramethylcyclopentadienyl)(3-tert-butyl-2-phenoxy)titanium dichloride, isopropylidene(tetramethylcyclopentadienyl)(3-tert-butyl-5-methyl-2-phenoxy)titanium dichloride, isopropylidene(tetramethylcyclopentadienyl)(3-phenyl-2-phenoxy)titanium dichloride, isopropylidene(tetramethylcyclopentadienyl)(3-tert-butyldimethylsilyl-5-methyl-2-phenoxy)titanium dichloride, isopropylidene(tetramethylcyclopentadienyl)(3-trimethylsilyl-5-methyl-2-phenoxy)titanium dichloride, isopropylidene(tetramethylcyclopentadienyl)(3-tert-butyl-5-methoxy-2-phenoxy)titanium dichloride, isopropylidene(tetramethylcyclopentadienyl)(3-tert-butyl-5-chloro-2-phenoxy)titanium dichloride, isopropylidene(trimethylsilylcyclopentadienyl)(3,5-dimethyl-2-phenoxy)titanium dichloride, isopropylidene(trimethylsilylcyclopentadienyl)(3-tert-butyl-2-phenoxy)titanium dichloride, isopropylidene(trimethylsilylcyclopentadienyl)(3-tert-butyl-5-methyl-2-phenoxy)titanium dichloride, isopropylidene(trimethylsilylcyclopentadienyl)(3-phenyl-2-phenoxy)titanium dichloride, isopropylidene(trimethylsilylcyclopentadienyl)(3-tert-butyldimethylsilyl-5-methyl-2-phenoxy)titanium dichloride, isopropylidene(trimethylsilylcyclopentadienyl)(3-trimethylsilyl-5-methyl-2-phenoxy)titanium dichloride, isopropylidene(trimethylsilylcyclopentadienyl)(3-tert-butyl-5-methoxy-2-phenoxy)titanium dichloride, isopropylidene(trimethylsilylcyclopentadienyl)(3-tert-butyl-5-chloro-2-phenoxy)titanium dichloride, isopropylidene(fluorenyl)(3,5-dimethyl-2-phenoxy)titanium dichloride, isopropylidene(fluorenyl)(3-tert-butyl-2-phenoxy)titanium dichloride, isopropylidene(fluorenyl)(3-tert-butyl-5-methyl-2-phenoxy)titanium dichloride, isopropylidene(fluorenyl)(3-phenyl-2-phenoxy)titanium dichloride, isopropylidene(fluorenyl)(3-tert-butyldimethylsilyl-5-methyl-2-phenoxy)titanium dichloride, isopropylidene(fluorenyl)(3-trimethylsilyl-5-methyl-2-phenoxy)titanium dichloride, isopropylidene(fluorenyl)(3-tert-butyl-5-methoxy-2-phenoxy)titanium dichloride, isopropylidene(fluorenyl)(3-tert-butyl-5-chloro-2-phenoxy)titanium dichloride, diphenylmethylene(cyclopentadienyl)(3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethylsilyl-5-methyl-2-phenoxy)titanium dichloride, diphenylmethylene(cyclopentadienyl)(3-trimethylsilyl-5-methyl-2-phenoxy)titanium dichloride, diphenylmethylene(cyclopentadienyl)(3-tert-butyl-5-methoxy-2-phenoxy)titanium dichloride, diphenylmethylene(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene(methylcyclopentadienyl)(3-tert-butyldimethylsilyl-5-methyl-2-phenoxy)titanium dichloride, diphenylmethylene(methylcyclopentadienyl)(3-trimethylsilyl-5-methyl-2-phenoxy)titanium dichloride, diphenylmethylene(methylcyclopentadienyl)(3-tert-butyl-5-methoxy-2-phenoxy)titanium dichloride, diphenylmethylene(methylcyclopentadienyl)(3-tert-butyl-5-chloro-2-phenoxy)titanium dichloride, diphenylmethylene(t-butylcyclopentadienyl)(3,5-dimethyl-2-phenoxy)titanium dichloride, diphenylmethylene(t-butylcyclopentadienyl)(3-tert-butyl-2-phenoxy)titanium dichloride, diphenylmethylene(t-butylcyclopentadienyl)(3-tert-butyl-5-methyl-2-phenoxy)titanium dichloride, diphenylmethylene(t-butylcyclopentadienyl)(3-phenyl-2-phenoxy)titanium dichloride, diphenylmethylene(t-butylcyclopentadienyl)(3-tert-butyldimethylsilyl-5-methyl-2-phenoxy)titanium dichloride, diphenylmethylene(t-butylcyclopentadienyl)(3-trimethylsilyl-5-methyl-2-phenoxy)titanium dichloride, diphenylmethylene(t-butylcyclopentadienyl)(3-tert-butyl-5-methoxy-2-phenoxy)titanium dichloride, diphenylmethylene(t-butylcyclopentadienyl)(3-tert-butyl-5-chloro-2-phenoxy)titanium dichloride, diphenylmethylene(tetramethylcyclopentadienyl)(3,5-dimethyl-2-phenoxy)titanium dichloride, diphenylmethylene (tetramethylcyclopentadienyl)(3-tert-butyl-2-phenoxy) titanium dichloride, diphenylmethylene(tetramethylcyclopentadienyl)(3-tert-butyl-5-methyl-2-phenoxy)titanium dichloride, diphenylmethylene(tetramethylcyclopentadienyl)(3-phenyl-2-phenoxy) titanium dichloride, diphenylmethylene(tetramethylcyclopentadienyl)(3-tert-butyldimethylsilyl-5-methyl-2-phenoxy)titanium dichloride, diphenylmethylene(tetramethylcyclopentadienyl)(3-trimethylsilyl-5-methyl-2-phenoxy)titanium dichloride, diphenylmethylene(tetramethylcyclopentadienyl)(3-tert-butyl-5-methoxy-2-phenoxy)titanium dichloride, diphenylmethylene(tetramethylcyclopentadienyl)(3-tert-butyl-5-chloro-2-phenoxy)titanium dichloride, diphenylmethylene(trimethylsilylcyclopentadienyl)(3,5-dimethyl-2-phenoxy) titanium dichloride, diphenylmethylene(trimethylsilylcyclopentadienyl)(3-tert-butyl-2-phenoxy) titanium dichloride, diphenylmethylene(trimethylsilylcyclopentadienyl)(3-tert-butyl-5-methyl-2-phenoxy)titanium dichloride, diphenylmethylene(trimethylsilylcyclopentadienyl)(3-phenyl-2-phenoxy) titanium dichloride, diphenylmethylene(trimethylsilylcyclopentadienyl)(3-tert-butyldimethylsilyl-5-methyl-2-phenoxy)titanium dichloride, diphenylmethylene(trimethylsilylcyclopentadienyl)(3-trimethylsilyl-5-methyl-2-phenoxy)titanium dichloride, diphenylmethylene(trimethylsilylcyclopentadienyl)(3-tert-butyl-5-methoxy-2-phenoxy)titanium dichloride, diphenylmethylene(trimethylsilylcyclopentadienyl)(3-tert-butyl-5-chloro-2-phenoxy)titanium dichloride, diphenylmethylene(fluorenyl)(3,5-dimethyl-2-phenoxy) titanium dichloride, diphenylmethylene(fluorenyl)(3-tert-butyl-2-phenoxy)titanium dichloride, diphenylmethylene(fluorenyl)(3-tert-butyl-5-methyl-2-phenoxy)titanium dichloride, diphenylmethylene(fluorenyl)(3-phenyl-2-phenoxy)titanium dichloride, diphenylmethylene(fluorenyl)(3-tert-butyldimethylsilyl-5-methyl-2-phenoxy)titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride, diphenylmethylene(fluorenyl)(3-tert-butyl-5-chloro-2-phenoxy)titaniumdichloride, compounds wherein titanium in these compounds is replaced by zirconium or hafnium, compounds wherein dichloride in these compounds replaced by dibromide, diiodide, bis(dimethylamide), bis(diethylamide), di-n-butoxide or diisopropoxide, compounds wherein (cyclopentadienyl) in these compounds replaced by (dimethylcyclopentadienyl), (trimethylcyclopentadienyl), (n-buylcyclopentadienyl), (tert-butyldimethylsilylcyclopentadienyl) or (indenyl), compounds wherein (3,5-dimethyl-2-phenoxy) in these compounds replaced by (2-phenoxy), (3-methyl-2-phenoxy), (3,5-di-tert-butyl-2-phenoxy), (3-phenyl-5-methyl-2-phenoxy), (3-tert-butyldimethylsilyl-2-phenoxy) or (3-trimethylsilyl-2-phenoxy), and the like.

Specific examples of the compound represented by the above-described general formula (3) include transition metal complexes such as dimethylsilylene(cyclopentadienyl)(2-phenoxy)titanium dichloride, dimethylsilylene(cyclopentadienyl)(3-methyl-2-phenoxy)titanium dichloride, dimethylsilylene(cyclopentadienyl)(3,5-dimethyl-2-phenoxy)titanium dichloride, dimethylsilylene(cyclopentadienyl)(3-tert-butyl-2-phenoxy)titanium dichloride, dimethylsilylene(cyclopentadienyl)(3-tert-butyl-5-methyl-2-phenoxy)titanium dichloride, dimethylsilylene(cyclopentadienyl)(3,5-di-tert-butyl-2-phenoxy)titanium dichloride, dimethylsilylene(cyclopentadienyl)(5-methyl-3-phenyl-2-phenoxy)titanium dichloride, dimethylsilylene(cyclopentadienyl)(3-tert-butyldimethylsilyl-5-methyl-2-phenoxy)titanium dichloride, dimethylsilylene(cyclopentadienyl)(5-methyl-3-trimethylsilyl-2-phenoxy) titanium dichloride, dimethylsilylene(cyclopentadienyl)(3-tert-butyl-5-methoxy-2-phenoxy)titanium dichloride, dimethylsilylene(cyclopentadienyl)(3-tert-butyl-5-chloro-2-phenoxy)titanium dichloride, dimethylsilylene(cyclopentadienyl)(3,5-diamyl-2-phenoxy)titanium dichloride, dimethylsilylene(methylcyclopentadienyl)(2-phenoxy)titanium dichloride, dimethylsilylene(methylcyclopentadienyl)(3-methyl-2-phenoxy)titanium dichloride, dimethylsilylene(methylcyclopentadienyl)(3,5-dimethyl-2-phenoxy)titanium dichloride, dimethylsilylene(methylcyclopentadienyl)(3-tert-butyl-2-phenoxy)titanium dichloride, dimethylsilylene(methylcyclopentadienyl)(3-tert-butyl-5-methyl-2-phenoxy)titanium dichloride, dimethylsilylene(methylcyclopentadienyl)(3,5-di-tert-butyl-2-phenoxy)titanium dichloride, dimethylsilylene(methylcyclopentadienyl)(5-methyl-3-phenyl-2-phenoxy) titanium dichloride, dimethylsilylene(methylcyclopentadienyl)(3-tert-butyldimethylsilyl-5-methyl-2-phenoxy)titanium dichloride, dimethylsilylene(methylcyclopentadienyl)(5-methyl-3-trimethylsilyl-2-phenoxy)titanium dichloride, dimethylsilylene(cyclopentadienyl)(3-tert-butyl-5-methoxy-2-phenoxy) titanium dichloride, dimethylsilylene(cyclopentadienyl)(3-tert-butyl-5-chloro-2-phenoxy)titanium dichloride, dimethylsilylene(cyclopentadienyl)(3,5-diamyl-2-phenoxy) titanium dichloride, dimethylsilylene(n-butylcyclopentadienyl)(2-phenoxy)titanium dichloride, dimethylsilylene(n-butylcyclopentadienyl)(3-methyl-2-phenoxy)titanium dichloride, dimethylsilylene(n-butylcyclopentadienyl)(3,5-dimethyl-2-phenoxy)titanium dichloride, dimethylsilylene(n-butylcyclopentadienyl)(3-tert-butyl-2-phenoxy)titanium dichloride, dimethylsilylene(n-butylcyclopentadienyl)(3-tert-butyl-5-methyl-2-phenoxy)titanium dichloride, dimethylsilylene(n-butylcyclopentadienyl)(3,5-di-tert-butyl-2-phenoxy) titanium dichloride, dimethylsilylene(n-butylcyclopentadienyl)(5-methyl-3-phenyl-2-phenoxy) titanium dichloride, dimethylsilylene(n-butylcyclopentadienyl)(3-tert-butyldimethylsilyl-5-methyl-2-phenoxy)titanium dichloride, dimethylsilylene(n-butylcyclopentadienyl)(5-methyl-3-trimethylsilyl-2-phenoxy)titanium dichloride, dimethylsilylene(n-butylcyclopentadienyl)(3-tert-butyl-5-methoxy-2-phenoxy) titanium dichloride, dimethylsilylene(n-butylcyclopentadienyl)(3-tert-butyl-5-chloro-2-phenoxy) titanium dichloride, dimethylsilylene(n-butylcyclopentadienyl)(3,5-diamyl-2-phenoxy)titanium dichloride, dimethylsilylene(tert-butylcyclopentadienyl)(2-phenoxy)titanium dichloride, dimethylsilylene(tert-butylcyclopentadienyl)(3-methyl-2-phenoxy)titanium dichloride, dimethylsilylene(tert-butylcyclopentadienyl)(3,5-dimethyl-2-phenoxy)titanium dichloride, dimethylsilylene(tert-butylcyclopentadienyl)(3-tert-butyl-2-phenoxy)titanium dichloride, dimethylsilylene(tert-butylcyclopentadienyl)(3-tert-butyl-5-methyl-2-phenoxy) titanium dichloride, dimethylsilylene(tert-butylcyclopentadienyl)(3,5-di-tert-butyl-2-phenoxy) titanium dichloride, dimethylsilylene(tert-butylcyclopentadienyl)(5-methyl-3-phenyl-2-phenoxy) titanium dichloride, dimethylsilylene(tert-butylcyclopentadienyl)(3-tert-butyldimethylsilyl-5-methyl-2-phenoxy)titanium dichloride, dimethylsilylene(tert-butylcyclopentadienyl)(5-methyl-3-trimethylsilyl-2- phenoxy)titanium dichloride, dimethylsilylene(tert-butylcyclopentadienyl)(3-tert-butyl-5-methoxy-2-phenoxy) titanium dichloride, dimethylsilylene(tert-butylcyclopentadienyl)(3-tert-butyl-5-chloro-2-phenoxy) titanium dichloride, dimethylsilylene(tert-butylcyclopentadienyl)(3,5-diamyl-2-phenoxy)titanium dichloride, dimethylsilylene(tetramethylcyclopentadienyl) (2-phenoxy)titanium dichloride, dimethylsilylene (tetramethylcyclopentadienyl)(3-methyl-2-phenoxy) titanium dichloride, dimethylsilylene (tetramethylcyclopentadienyl)(3,5-dimethyl-2-phenoxy) titanium dichloride, dimethylsilylene (tetramethylcyclopentadienyl)(3-tert-butyl-2-phenoxy) titanium dichloride, dimethylsilylene (tetramethylcyclopentadienyl)(3-tert-butyl-5-methyl-2-phenoxy)titanium dichloride, dimethylsilylene (tetramethylcyclopentadienyl)(3,5-di-tert-butyl-2-phenoxy) titanium dichloride, dimethylsilylene (tetramethylcyclopentadienyl)(5-methyl-3-phenyl-2-phenoxy)titanium dichloride, dimethylsilylene (tetramethylcyclopentadienyl)(3-tert-butyldimethylsilyl-5-methyl-2-phenoxy)titanium dichloride, dimethylsilylene (tetramethylcyclopentadienyl)(5-methyl-3-trimethylsilyl-2-phenoxy)titanium dichloride, dimethylsilylene (tetramethylcyclopentadienyl)(3-tert-butyl-5-methoxy-2-phenoxy)titanium dichloride, dimethylsilylene (tetramethylcyclopentadienyl)(3-tert-butyl-5-chloro-2-phenoxy)titanium dichloride, dimethylsilylene (tetramethylcyclopentadienyl)(3,5-diamyl-2-phenoxy) titanium dichloride, dimethylsilylene (trimethylsilylcyclopentadienyl)(2-phenoxy)titanium dichloride, dimethylsilylene (trimethylsilylcyclopentadienyl)(3-methyl-2-phenoxy) titanium dichloride, dimethylsilylene (trimethylsilylcyclopentadienyl)(3,5-dimethyl-2-phenoxy) titanium dichloride, dimethylsilylene (trimethylsilylcyclopentadienyl)(3-tert-butyl-2-phenoxy) titanium dichloride, dimethylsilylene (trimethylsilylcyclopentadienyl)(3-tert-butyl-5-methyl-2-phenoxy)titanium dichloride, dimethylsilylene (trimethylsilylcyclopentadienyl)(3,5-di-tert-butyl-2-phenoxy)titanium dichloride, dimethylsilylene (trimethylsilylcyclopentadienyl)(5-methyl-3-phenyl-2-phenoxy)titanium dichloride, dimethylsilylene (trimethylsilylcyclopentadienyl)(3-tert-butyldimethylsilyl-5-methyl-2-phenoxy)titanium dichloride, dimethylsilylene (trimethylsilylcyclopentadienyl)(5-methyl-3-trimethylsilyl-2-phenoxy)titanium dichloride, dimethylsilylene (trimethylsilylcyclopentadienyl)(3-tert-butyl-5-methoxy-2-phenoxy)titanium dichloride, dimethylsilylene (trimethylsilylcyclopentadienyl)(3-tert-butyl-5-chloro-2-phenoxy)titanium dichloride, dimethylsilylene (trimethylsilylcyclopentadienyl)(3,5-diamyl-2-phenoxy) titanium dichloride, dimethylsilylene(indenyl)(2-phenoxy) titaniumdichloride, dimethylsilylene(indenyl)(3-methyl-2-phenoxy)titanium dichloride, dimethylsilylene(indenyl)(3,5-dimethyl-2-phenoxy)titanium dichloride, dimethylsilylene(indenyl)(3-tert-butyl-2-phenoxy)titanium dichloride, dimethylsilylene(indenyl)(3-tert-butyl-5-methyl-2-phenoxy)titanium dichloride, dimethylsilylene(indenyl) (3,5-di-tert-butyl-2-phenoxy)titanium dichloride, dimethylsilylene(indenyl)(5-methyl-3-phenyl-2-phenoxy) titanium dichloride, dimethylsilylene(indenyl)(3-tert-butyldimethylsilyl-5-methyl-2-phenoxy)titanium dichloride, dimethylsilylene(indenyl)(5-methyl-3-trimethylsilyl-2-phenoxy)titanium dichloride, dimethylsilylene(indenyl)(3-tert-butyl-5-methoxy-2-phenoxy)titanium dichloride, dimethylsilylene(indenyl)(3-tert-butyl-5-chloro-2-phenoxy)titanium dichloride, dimethylsilylene(indenyl)(3,5-diamyl-2-phenoxy)titanium dichloride, dimethylsilylene(fluorenyl)(2-phenoxy)titanium dichloride, dimethylsilylene(fluorenyl)(3-methyl-2-phenoxy)titanium dichloride, dimethylsilylene(fluorenyl)(3,5-dimethyl-2-phenoxy)titanium dichloride, dimethylsilylene(fluorenyl)(3-tert-butyl-2-phenoxy) titanium dichloride, dimethylsilylene(fluorenyl)(3-tert-butyl-5-methyl-2-phenoxy)titanium dichloride, dimethylsilylene(fluorenyl)(3,5-di-tert-butyl-2-phenoxy) titanium dichloride, dimethylsilylene(fluorenyl)(5-methyl-3-phenyl-2-phenoxy)titanium dichloride, dimethylsilylene (fluorenyl)(3-tert-butyldimethylsilyl-5-methyl-2-phenoxy) titanium dichloride, dimethylsilylene(fluorenyl)(5-methyl-3-trimethylsilyl-2-phenoxy)titanium dichloride, dimethylsilylene(fluorenyl)(3-tert-butyl-5-methoxy-2-phenoxy)titanium dichloride, dimethylsilylene(fluorenyl)(3-tert-butyl-5-chloro-2-phenoxy)titanium dichloride, dimethylsilylene(fluorenyl)(3,5-dipentyl-2-phenoxy) titanium dichloride, dimethylsilylene (tetramethylcyclopentadienyl)(1-naphthoxy-2-yl)titanium dichloride, compounds wherein (cyclopentadienyl) in these compounds is replaced by (dimethylcyclopentadienyl), (trimethylcyclopentadienyl), (ethylcyclopentadienyl), (n-propylcyclopentadienyl), (isopropylcyclopentadienyl), (sec-butylcyclopentadienyl), (isobutylcyclopentadienyl), (tert-butyldimethylsilylcyclopentadienyl), (phenylcyclopentadienyl), (methylindenyl) or (phenylindenyl), compounds wherein (2-phenoxy) in these compounds is replaced by (3-phenyl-2-phenoxy), (3-trimethylsilyl-2-phenoxy) or (3-tert-butyldimethylsilyl-2-phenoxy), compounds wherein dimethylsilylene in these compounds is replaced by diphenylsilylene, divinylsilylene or dimethoxysilylene, compounds wherein titanium in these compounds is replaced by zirconium or hafnium, compounds wherein dichloride in these compounds is replaced by dibromide, diiodide, bis(dimethylamide), bis (diethylamide), di-n-butoxide or diisopropoxide, and the like.

Specific examples of the compound represented by the above-described general formula (4) include transition metal complexes such as bis(cyclopentadienyl)titanium dichloride, bis(methylcyclopentadienyl)titanium dichloride, bis(dimethylcyclopentadienyl)titanium dichloride, bis (trimethylcyclopentadienyl)titanium dichloride, bis (tetramethylcyclopentadienyl)titanium dichloride, bis (pentamethylcyclopentadienyl)titanium dichloride, bis (ethylcyclopentadienyl)titanium dichloride, bis (n-butylcyclopentadienyl)titanium dichloride, bis(tert-butylcyclopentadienyl)titanium dichloride, bis(indenyl )titanium dichloride, bis (tetrahydroindenyl )titanium dichloride, (cyclopentadienyl)(fluorenyl)titanium dichloride, (cyclopentadienyl)(dimethylfluorenyl)titanium dichloride, (dimethylcyclopentadienyl)(fluorenyl)titanium dichloride, (indenyl)(fluorenyl)titanium dichloride, compounds wherein titanium in these compounds is replaced by zirconium or hafnium, compounds wherein dichloride in these compounds is replaced by diiodide, bis (dimethylamide), bis(diethylamide), di-n-butoxide or diisopropoxide, and the like.

Specific examples of the compound represented by the above-described general formula (5) include transition metal compounds such as (dimethylamide)(cyclopentadienyl) titanium dichloride, (diethylamide)(cyclopentadienyl) titanium dichloride, (di-n-propylamide)(cyclopentadienyl) titanium dichloride, (diisopropylamide)(cyclopentadienyl)

titaniumdichloride, (di-t-butylamide)(cyclopentadienyl) titanium dichloride, (diphenylamide)(cyclopentadienyl) titanium dichloride, (dicyclohexylamide)(cyclopentadienyl) titanium dichloride, (cyclopentadienyl)(pyrrolidinyl) titanium dichloride, (cyclopentadienyl)(piperidinyl)titanium dichloride, (cyclopentadienyl)(phospholanyl)titanium dichloride, (cyclopentadienyl)(phosphanyl)titanium dichloride, compounds wherein cyclopentadienyl in these compounds is replaced by methylcyclopentadienyl, dimethylcyclopentadienyl, trimethylcyclopentadienyl, tetramethylcyclopentadienyl, pentamethylcyclopentadienyl, ethylcyclopentadienyl, n-propylcyclopentadienyl, isopropylcyclopentadienyl, sec-butylcyclopentadienyl, isobutylcyclopentadienyl, tert-butylcyclopentadienyl, di-tert-butylcyclopentadienyl, tert-butyldimethylsilylcyclopentadienyl, phenylcyclopentadienyl, methylindenyl or phenylindenyl, compounds wherein titanium in these compounds is replaced by zirconium or hafnium, and compounds wherein dichloride in these compounds is replaced by dibromide, diiodide, bis(dimethylamide), bis(diethylamide), dimethoxide, di-n-butoxide, diisopropoxide or diphenoxide, and the like.

The transition metal complexes represented by the general formulas (1) to (5) are produced, for example, by reacting a cyclopentadiene compound as a ligand precursor with a strong base, then, reacting the reaction product with a transition metal compound such as a halogenated compound of a transition metal. Further, the transition metal complexes represented by the general formula (1) to (5) can be obtained also by reacting the reaction product with an organoalkaline metal compound such as methyllithium and the like.

As the strong base, an organoalkaline metal compound, hydrogenated compound of alkaline metal, organomagnesium compound or the like is often used.

The addition order of these reagents in these reactions is not particularly restricted.

The reaction temperature is usually −100° C. or more and not more than the boiling point of the solvent, and preferably in the range from −80 to 150° C. In usual, since the material of an apparatus used is restricted industrially and the load of production cost such as a refrigerant and the like increases in the case of the reaction at lower temperature such as −80° C. and −40° C., the reaction is preferably conducted in the range from −20 to 150° C. which is industrially advantageous.

The reaction of a ligand precursor with a strong base is effective that the reaction is initiated at a low temperature of not more than 50° C. and the reaction is carried out with keeping the temperature constant or gradually increasing the temperature since this reaction is generally an exothermic reaction and the strong base used and the produced salt may sometimes be decomposed at high temperature depending on the solvent used. Further, since also the reaction with a transition metal compound such as a transition metal halide compound is generally an exothermic reaction and the produced salt may sometimes be decomposed at high temperature range depending on the solvent used, it is effective that the reaction is initiated at a low temperature of not more than 50° C. and the reaction is carried out with keeping the temperature constant or gradually elevating the temperature as described above.

The above-described reaction is usually conducted in an inert solvent. More specifically, it can be generally effected in the presence of an aromatic hydrocarbon solvent such as benzene, toluene, xylene, mesitylene, chlorobenzene, dichlorobenzene or the like; an aliphatic hydrocarbon solvent such as pentane, hexane, heptane, octane, petroleum ether or the like; an ether solvent such as tetrahydrofuran, dioxane, diethyl ether, diisopropyl ether, dimethoxyethane or the like; or a halogenated hydrocarbon solvent such as dichloromethane, dichloroethane or the like.

Among them, when an ether solvent such as tetrahydrofuran or the like, or a halogenated hydrocarbon solvent such as dichloromethane or the like is used, for example, a salt such as lithium chloride or the like by-produced is sometimes unfavorably dissolved in the solvent and mixed into an intended compound in purification. In this case, the intended compound and the salt can be separated by solvent substitution, however, it increases the number of production steps. Though a solvent such as diethyl ether can control the above-described mixing of lithium chloride and the like, the boiling point thereof is lower for industrial application, and for some transition metal compounds, when an ether solvent is used, a metal-ether bond is produced by the reaction of a center metal with an ether solvent, therefore, the use of an ether solvent may sometimes be undesirable. Accordingly, it is more preferable to use an aliphatic hydrocarbon solvent or an aromatic hydrocarbon solvent, and the subsequent purification operation can be carried out after removing a by-product quickly by filtration or the like without solvent substitution.

EXAMPLES

The following examples further illustrate the present invention specifically, but do not limit the present invention.

Example 1

Into a 100 ml four-necked flask equipped with a stirrer was charged a solution composed of 9.51 g (26.7 mmol) of (3-tert-butyl-2-methoxy-5-methylphenyl)(2,3,4,5-tetramethylcyclopentadienyl)dimethylsilane, 38 g of toluene and 5.93 g (58.7 mmol) of triethylamine under nitrogen atmosphere, to this was added dropwise 18.0 ml of a 1.63M solution of n-butyllithium in hexane at 15° C. over 4 hours slowly, and the mixture was stirred for 12 hours at 15° C. This reaction solution was added over 2 hours to a solution separately prepared by dissolving 5.58 g (29.4 mmol) of $TiCl_4$ in 38 g of toluene under nitrogen atmosphere and then cooling to −10° C. The resulted reaction solution was heated slowly to room temperature over 1.5 hours, and further heated to the reflux temperature over 1 hour and refluxed for 10 hours. The solution changed to brownish color, and a solid of brownish color was deposited. This was filtered through celite, the resulted solid was extracted twice using 20 g of toluene per one operation. The extracted solutions and filtrates were combined, and concentrated to 19 g, and the concentrated solution was heated to 50° C., and to this was added 60.9 g of hexane while stirring, and the solution was cooled slowly (10° C./hr) to −10° C. while stirring, then stirred for 12 hours to deposit a yellow powder. Thusobtained yellow powder was filtered, washed with hexane, then, dried under reduced pressure to obtain 2.63 g of a yellow powder. Further, the filtrate was concentrated to 10 g, to this was added 31 g of hexane at 50° C., the mixture was cooled slowly (10° C./hr) to −10° C. with stirring to obtain further 1.47 g of a purified yellow powder. The $^1$H-NMR ($CDCl_3$ solution) data of this yellow powder are shown below.

δ 0.57(s, 6H), 1.41(s, 9H), 2.15(s, 6H), 2.34(s, 6H), 2.38 (s, 3H), 6.17(t, 2H), 7.15(s, 1H), 7.18(s, 1H); The $^{13}$C-NMR ($CDCl_3$ solution) data are shown below. δ 1.25, 14.48, 16.28, 22.47, 31.25, 36.29, 120.23, 130.62, 131.47, 133.86, 135.50, 136,37, 140.82, 142.28, 167.74; Mass spectrum (CI, m/e)458.

From the $^1$H-NMR (CDCl$_3$ solution) date, $^{13}$C-NMR (CDCl$_3$ solution) data and mass spectrum data, the resulted yellow powder was recognized as dimethylsilylene (tetramethylcyclopentadienyl)(3-tert-butyl-5-methyl-2-phenoxy)titanium dichloride (yield 33.4%).

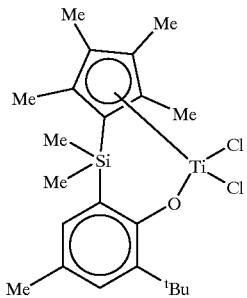

Example 2

Into a 100 ml four-necked flask equipped with a stirrer was charged a solution composed of 9.51 g (26.7 mmol) of (3-tert-butyl-2-methoxy-5-methylphenyl)(2,3,4,5-tetramethylcyclopentadienyl)dimethylsilane, 38 g of toluene and 5.93 g (58.7 mmol) of triethylamine under nitrogen atmosphere, to this was added dropwise 18.0 ml of a 1.63M solution of n-butyllithium in hexane at 15° C. over 4 hours slowly, and the mixture was stirred for 12 hours at 15° C. This reaction solution was added to a solution over 2 hours which had been separately prepared by dissolving 5.58 g (29.4 mmol) of TiCl$_4$ in 38 g of toluene under nitrogen atmosphere and cooling the mixture down to −10° C. The resulted reaction solution was heated slowly to room temperature over 1.5 hours, and further heated to the reflux temperature over 1 hour and ref luxed for 10 hours. The solution changed to brownish color, and a solid of brownish color was deposited. This was filtered through celite, the resulted solid was extracted twice using 20 g of toluene per one operation. The extracted solutions and filtrates were combined, and concentrated to 19 g, and the concentrated solution was heated to 50° C., and the solution was cooled slowly (10° C./hr) to −10° C. with stirring, then stirred for 12 hours to deposit a yellow powder. This was filtered, washed with hexane, then, dried under reduced pressure to obtain 2.52 g of a yellow powder. Further, the filtrate was concentrated to 12 g at 50° C., then, the mixture was cooled slowly to −10° C. with stirring to obtain further 1.35 g of a yellow powder. The resulted yellow powder was recognized as dimethylsilylene (tetramethylcyclopentadienyl)(3-tert-butyl-5-methyl-2-phenoxy)titanium dichloride (yield 31.6%) since it showed the same spectra as those of the powder obtained in Example 1 as a result of the spectroscopic analysis.

Comparative Example 1

Into a 100 ml four-necked flask equipped with a stirrer was charged a solution composed of 9.51 g (26.7 mmol) of (3-tert-butyl-2-methoxy-5-methylphenyl)(2,3,4,5-tetramethylcyclopentadienyl)dimethylsilane, 38 g of toluene and 5.93 g (58.7 mmol) of triethylamine under nitrogen atmosphere, to this was added dropwise 18.0 ml of a 1.63M solution of n-butyllithium in hexane at 15° C. over 4 hours slowly, and the mixture was stirred for 12 hours at 15° C. This reaction solution was added over 2 hours to a solution separately prepared by dissolving 5.58 g (29.4 mmol) of TiCl$_4$ in 38 g of toluene under nitrogen atmosphere and cooling the mixture down to −10° C. The resulted reaction solution was heated slowly to room temperature over 1.5 hours, and further heated to the reflux temperature over 1 hour and refluxed for 10 hours. The solution changed to brownish color, and a solid of brownish color was deposited. This was filtered through celite, the resulted solid was extracted twice using 20 g of toluene per one operation. The extracted solutions and filtrates were combined, and concentrated to 19 g, and the concentrated solution was heated to 50° C. with stirring, and to this was added 60.9 g of hexane, and the solution was cooled slowly (10° C./hr) to −10° C., then allowed to stand still for 12 hours to deposit a yellow column crystal onto the wall surface of the flask. This was filtered by decantation, washed with hexane, then, dried under reduced pressure to obtain 2.54 g of a yellow column crystal. Further, the filtrate was concentrated to 10 g, to this was added 31 g of hexane at 50° C., the mixture was cooled slowly (10° C./hr) to −10° C. to obtain further 1.51 g of a yellow column crystal. The resulted yellow column crystal was recognized as dimethylsilylene (tetramethylcyclopentadienyl)(3-tert-butyl-5-methyl-2-phenoxy)titanium dichloride (yield 33.0%) since it showed the same spectra as those of the powder obtained in Example 1 as a result of the spectroscopic analyses.

Though the intended compound was obtained in the same yield as that in Example 1, the compound was deposited onto the wall surface and a process for scraping it was necessary.

Example 3

Into a 500 ml four-necked flask equipped with a stirrer was charged a solution composed of 18.12 g (72.19 mmol) of (tert-butylamide)(2,3,4,5-tetramethylcyclopentadienyl) dimethylsilane, 91 g of toluene and 30.46 g (301.6 mmol) of triethylamine under nitrogen atmosphere, to this was added dropwise 98.4 ml of a 1.54M solution of n-butyllithium in hexane at 5° C. over 4 hours slowly, and the mixture was stirred for 12 hours at 15° C. A uniform solution was obtained. To this solution cooled to −10° C. was added a solution over 2 hours slowly which had been separately prepared by dissolving 14.40 g (75.79 mmol) of TiCl$_4$ in 45 g of toluene under nitrogen atmosphere and cooling the mixture down to −10° C. The resulted reaction solution was heated slowly to room temperature over 1.5 hours, and further stirred overnight. This was filtered through celite, the resulted solid was extracted twice using 30 g of toluene per one operation. The filtrates and extracted solutions were combined, and concentrated to 26 g, and to this was added 105 g of hexane with stirring, and the solution was heated to 50° C. and cooled slowly (10° C./hr) to −10° C., then stirred for 12 hours to deposit a brown powder. This was filtered, washed with hexane, then, dried under reduced pressure to obtain 6.83 g of a brown powder. Further, the filtrate was concentrated to 17 g at 50° C., to this was added 68 g of hexane, the mixture was cooled slowly (10° C./hr) to −10° C. to obtain further 3.52 g of a brown powder. The $^1$H-NMR (CDCl$_3$ solution) date and mass spectrum data of this brown powder is shown below.

δ 0.71 (s, 6H), 1.44 (s, 9H), 2.14 (s, 6H), 2.24 (s, 6H) Mass spectrum (CI, m/e)367.

From the $^1$H-NMR (CDCl$_3$ solution) date and mass spectrum data, the resulted brown plate crystal was identified as dimethylsilylene(tert-butylamide) (teteramethylcyclopentadienyl)titanium dichloride (yield 39.0%).

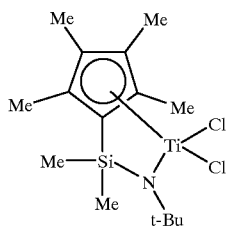

Comparative Example 2

Into a 100 ml four-necked flask equipped with a stirrer was charged a solution composed of 2.00 g (7.97 mmol) of (tert-butylamide)(2,3,4,5-tetramethylcyclopentadienyl) dimethylsilane, 10 g of toluene and 3.38 g (33.7 mmol) of triethylamine under nitrogen atmosphere, to this was added dropwise 10.6 ml of a 1.63M solution of n-butyllithium in hexane at 5° C. over 4 hours slowly, and the mixture was stirred for 12 hours at 15° C. A uniform solution was obtained. To this solution cooled to −10° C. was added a solution over 2 hours slowly which had been separately prepared by dissolving 1.62 g (8.53 mmol) of $TiCl_4$ in 5.0 g of toluene under nitrogen atmosphere and cooling the mixture down to −10° C. The resulted reaction solution was heated slowly to room temperature over 1.5 hours, and further stirred overnight. This was filtered through celite, the resulted solid was extracted twice using 10 g of toluene per one operation. The filtrates and extracted solutions were combined, then the solvent is distilled off, to this was added hexane, then the mixture was allowed to stand still, and cooled to deposit a brown plate crystal on the inner wall surface of the flask. The amount of the crystal collected and weighed was 1.11 g. The resulted brown plate crystal was recognized as dimethylsilylene(tert-butylamide) (tetramethylcyclopentadienyl)titanium dichloride (yield 37.8%) since it showed the same spectra as those in Example 3 as a result of the spectroscopic analysis.

Example 4

Into a 100 ml four-necked flask equipped with a stirrer was charged a solution composed of 1.59 g (4.02 mmol) of (cyclopentadienyl)(fluorenyl)diphenylmethane and 14.2 g of tetrahydrofuran under nitrogen atmosphere, to this was added dropwise 8.42 ml of a 1.05M solution of methyllithium in diethyl ether at 5° C. over 0.5 hours slowly, and the mixture was stirred for 5 hours at 15° C. The solvent was distilled off under reduced pressure to obtain a solid, and the solid was washed three times with 15 g of hexane to obtain 1.58 g of a reddish brown powder. Then, separately, a solution was prepared by suspending 0.95 g (4.1 mmol) of $ZrCl_4$ in 12 g of toluene under nitrogen atmosphere. Then, to a solution obtained by dissolving the reddish brown powder previously synthesized into 35 g of toluene in a 100 ml four-necked flask was added slowly the $ZrCl_4$ solution at 15° C. over 0.5 hours. This reaction solution was stirred over night, then, further reacted for 2 hours at 60° C. This reaction mixture was filtered through celite, the remaining solid was extracted twice using 8 g of toluene per one operation. The filtrates and extracted solutions were combined, and concentrated to 4.3 g at 50° C., and to this was added 9.5 g of hexane with stirring, and the solution was cooled slowly (10° C./hr) from 50° C. to −10° C., then stirred for 12 hours to deposit an orange powder. This was filtered, washed with hexane, then, dried under reduced pressure to obtain 1.1 g of an orange powder. Further, the filtrate was concentrated to 2.0 g at 50° C., then, to this was added 3.8 g of hexane while stirring, the mixture was cooled slowly to −15° C. to obtain further 0.6 g of an orange powder. The $^1$H-NMR ($CDCl_3$ solution) data and mass spectrum data of this orange powder are shown below.

δ 5.74 (t, 2H), 6.31 (t, 2H), 6.93 (dd, 2H), 7.25 (t, 2H), 7.29 (t, 2H), 7.40 (dt, 2H), 7.50 (t, 2H), 7.80 (d, 2H), 7,87 (d, 2H), 8.13 (dd, 2H); Mass spectrum (CI, m/e)556.

From the $^1$H-NMR ($CDCl_3$ solution) data and mass spectrum data, the resulted brown plate crystal was identified as diphenylmethylene(cyclopentadienyl)(fluorenyl) zirconium dichloride (yield 79.0%).

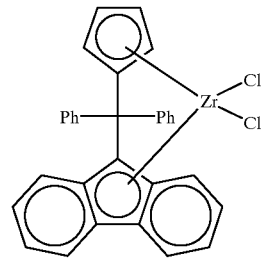

According to the present invention, it is possible to purify and produce a transition metal compound at high purity and efficiently under industrially and economically advantageous conditions.

What is claimed is:

1. A method for purifying a transition metal compound, which comprises concentrating a solution containing a transition metal compound, and then crystallizing a transition metal compound from a concentrated solution while stirring.

2. A method for purifying a transition metal compound, which comprises adding a poor solvent to a solution containing a transition metal compound, and conducting crystallization of the transition metal compound from the resulting mixture while stirring.

3. The method for purifying a transition metal compound according to claim 2, wherein the solution containing a transition metal compound is concentrated prior to addition of the poor solvent.

4. The method for purifying a transition metal compound according to claim 1, wherein the stirring is conducted under cooling.

5. The method for purifying a transition metal compound according to claim 2, wherein the stirring is conducted under cooling.

6. The method for purifying a transition metal compound according to claim 1, wherein the transition metal compound is a compound of a transition metal of III to IV Groups in the Periodic Table of Elements.

7. The method for purifying a transition metal compound according to claim 2, wherein the transition metal compound is a compound of a transition metal of III to IV Groups in the Periodic Table of Elements.

8. The method for purifying a transition metal compound according to claim 1, wherein the transition metal compound is a transition metal complex having a group having at least one cyclopentadiene type anion skeleton.

9. The method for purifying a transition metal compound according to claim 2, wherein the transition metal compound is a transition metal complex having a group having at least one cyclopentadiene type anion skeleton.

10. The method for purifying a transition metal compound according to claim 8, wherein the transition metal complex is a member selected from the group consisting of transition metal compounds represented by the following general formulas (1) to (5):

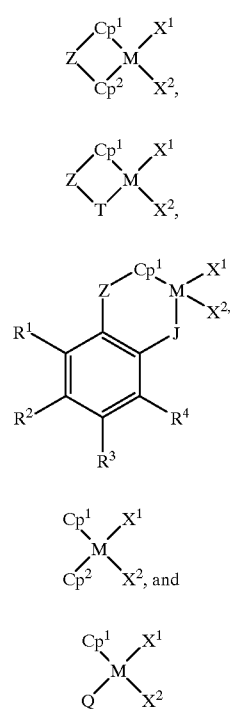

(wherein M represents a transition metal atom of IV Group in the Periodic Table of Elements; $Cp^1$ and $Cp^2$ represent each independently a group having a cyclopentadiene type anion skeleton; $X^1$, $X^2$, $R^1$, $R^2$, $R^3$ and $R^4$ represent each independently a hydrogen atom, a halogen atom, an alkyl group having 1 to 20 carbon atoms, an aralkyl group having 7 to 20 carbon atoms, an aryl group having 6 to 20 carbon atoms, a silyl group having 1 to 20 carbon atoms, an alkoxy group having 1 to 20 carbon atoms, an aralkyloxy group having 7 to 20 carbon atoms, an aryloxy group having 6 to 20 carbon atoms or an amino group having 2 to 20 carbon atoms; $R^1$, $R^2$, $R^3$ and $R^4$ may optionally be connected to form a ring; Z represents a divalent group represented by $SiR'_2$, $CR'_2$, $SiR'_2SiR'_2$, $CR'_2CR'_2$, $CR'=CR'$, $CR'_2SiR'_2$, $GeR'_2$ or $BR'$ (wherein, R' represents, in each case, a hydrogen atom, a halogen atom, an alkyl group having 1 to 20 carbon atoms, an alkenyl group having 2 to 20 carbon atoms, an aralkyl group having 7 to 20 carbon atoms, an aryl group having 6 to 20 carbon atoms, a silyl group having 1 to 20 carbon atoms, an alkoxy group having 1 to 20 carbon atoms, an aralkyloxy group having 7 to 20 carbon atoms, an aryloxy group having 6 to 20 carbon atoms which may be substituted or an amino group having 2 to 20 carbon atoms, when there are a plurality of R's, they may be combined to make a ring); and T represents a divalent group represented by —O—, —S—, —$NR^5$— or —$PR^6$— (wherein, $R^5$ and $R^6$ represent each independently an alkyl group having 1 to 20 carbon atoms, an aralkyl group having 7 to 20 carbon atoms, an aryl group having 6 to 20 carbon atoms or a silyl group having 1 to 20 carbon atoms); J represents an atom of XVI Group in the Periodic Table of Elements; and Q represents —$OR^7$, —$SR^8$, —$NR^9R^{10}$, or $PR^{11}R^{12}$ (wherein $R^7$, $R^8$, $R^9$, $R^{10}$, $R^{11}$ and $R^{12}$ represent each independently an alkyl group having 1 to 20 carbon atoms, an aralkyl group having 7 to 20 carbon atoms, an aryl group having 6 to 20 carbon atoms or a silyl group having 1 to 20 carbon atoms)).

11. The method for purifying a transition metal compound according to claim 1, wherein the transition metal complex is a member selected from the group consisting of transition metal complexes represented by the following general formulas (1) to (5):

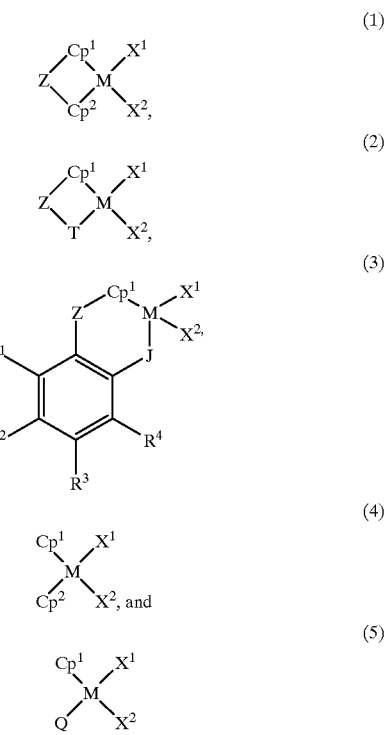

(wherein M represents a transition metal atom of IV Group in the Periodic Table of Elements; $Cp^1$ and $Cp^2$ represent each independently a group having a cyclopentadiene type anion skeleton; $X^1$, $X^2$, $R^1$, $R^2$, $R^3$ and $R^4$ represent each independently a hydrogen atom, a halogen atom, an alkyl group having 1 to 20 carbon atoms, an aralkyl group having 7 to 20 carbon atoms, an aryl group having 6 to 20 carbon atoms, a silyl group having 1 to 20 carbon atoms, an alkoxy group having 1 to 20 carbon atoms, an aralkyloxy group having 7 to 20 carbon atoms, an aryloxy group having 6 to 20 carbon atoms or an amino group having 2 to 20 carbon atoms; $R^1$, $R^2$, $R^3$ and $R^4$ may optionally be connected to form a ring; Z represents a divalent group represented by $SiR'_2$, $CR'_2$, $SiR'_2SiR'_2$, $CR'_2CR'_2$, $CR'=CR'$, $CR'_2SiR'_2$, $GeR'_2$ or $BR'$ (wherein, R' represents, in each case, a hydrogen atom, a halogen atom, an alkyl group having 1 to 20 carbon atoms, an alkenyl group having 2 to 20 carbon atoms, an aralkyl group having 7 to 20 carbon atoms, an aryl group having 6 to 20 carbon atoms, a silyl group having 1 to 20 carbon atoms, an alkoxy group having 1 to 20 carbon atoms, an aralkyloxy group having 7 to 20 carbon atoms, an aryloxy group having 6 to 20 carbon atoms which may be substituted or an amino group having 2 to 20 carbon atoms, when there are a plurality of R's, they may be combined to make a ring); and T represents a divalent group represented by —O—, —S—, —$NR^5$— or —$PR^6$—(wherein, $R^5$ and $R^6$ represent each independently an alkyl group having 1 to 20 carbon atoms, an aralkyl group having 7 to 20 carbon atoms, an aryl group having 6 to 20 carbon atoms or a silyl group having 1 to 20 carbon atoms); J represents an atom of XVI Group in the Periodic Table of Elements; and Q represents —$OR^7$, —$SR^8$, —$NR^9R^{10}$, or $PR^{11}R^{12}$ (wherein $R^7$, $R^8$, $R^9$, $R^{10}$, $R^{11}$ and $R^{12}$ represent each independently an alkyl group having 1 to 20 carbon atoms, an aralkyl group having 7 to 20 carbon atoms, an aryl group having 6 to 20 carbon atoms or a silyl group having 1 to 20 carbon atoms)).

12. The method for purifying a transition metal compound according to claim 10, wherein Z represents a divalent group represented by $SiR'_2$, $CR'_2$ or $CR'_2CR'_2$ (wherein R' means as defined above).

13. The method for purifying a transition metal compound according to claim 11, wherein Z represents a divalent group represented by $SiR'_2$, $CR'_2$ or $CR'_2CR'_2$ (wherein R' means as defined above).

14. The method for purifying a transition metal compound according to claim 10, wherein $X^1$ and $X^2$ represent each independently a halogen atom, an alkyl group having 1 to 20 carbon atoms, an aralkyl group having 7 to 20 carbon atoms, an aryl group having 6 to 20 carbon atoms or an alkoxy group having 1 to 10 carbon atoms.

15. A process of producing a purified transition metal complex, comprising the steps of:

forming a transition metal complex by reacting a cyclopentadiene compound ligand precursor with a strong base to give a reaction product, and reacting the reaction product with either (i) a transition metal compound, or (ii) an organoalkaline metal compound, thereby to form said metal complex; and concentrating a solution containing the so formed transition metal complex, and then crystallizing the so formed transition metal complex from the concentrated solution while stirring said concentrated solution.

16. A process of producing a purified transition metal complex, comprising the steps of:

forming a transition metal complex by reacting a cyclopentadiene compound as a ligand precursor with a strong base to give a reaction product, and reacting the product with either (i) a transition metal compound, or (ii) an organoalkaline metal compound, thereby to form said metal complex; and adding a poor solvent to a solution containing the so formed transition metal complex, and then crystallizing the so formed transition metal complex from the solution while stirring said solution mixture.

* * * * *